United States Patent
Auld et al.

(10) Patent No.: US 9,393,370 B2
(45) Date of Patent: Jul. 19, 2016

(54) VISCOUS FLUID INJECTOR

(71) Applicant: Ataviz LLC, Irvine, CA (US)

(72) Inventors: Jack R Auld, Laguna Niguel, CA (US); John C Huculak, Mission Viejo, CA (US); Matthew McCawley, San Clemente, CA (US)

(73) Assignee: ALTAVIZ LLC, Irvine, CA (US)

( * ) Notice: Subject to any disclaimer, the term of this patent is extended or adjusted under 35 U.S.C. 154(b) by 171 days.

(21) Appl. No.: 13/899,439

(22) Filed: May 21, 2013

(65) Prior Publication Data

US 2013/0317478 A1 Nov. 28, 2013

Related U.S. Application Data

(60) Provisional application No. 61/651,488, filed on May 24, 2012.

(51) Int. Cl.
| | |
|---|---|
| *A61M 1/00* | (2006.01) |
| *A61M 5/48* | (2006.01) |
| *A61M 5/20* | (2006.01) |
| *A61F 9/00* | (2006.01) |

(52) U.S. Cl.
CPC .............. *A61M 5/482* (2013.01); *A61F 9/0017* (2013.01); *A61M 5/2046* (2013.01)

(58) Field of Classification Search
CPC .... A61M 5/482; A61M 5/2046; A61F 9/0017
See application file for complete search history.

(56) References Cited

U.S. PATENT DOCUMENTS

| | | | |
|---|---|---|---|
| 2,547,099 A | 4/1951 | Smoot | |
| 2,605,763 A | 8/1952 | Smoot | |
| 4,940,460 A | 7/1990 | Casey et al. | |
| 4,941,880 A | 7/1990 | Burns | |
| 5,019,037 A | 5/1991 | Wang et al. | |
| 5,024,656 A | 6/1991 | Gasaway et al. | |
| 6,997,904 B2 | 2/2006 | Sculati | |
| 7,195,610 B1 | 3/2007 | Flachbart | |
| 7,601,140 B2 | 10/2009 | Rossback et al. | |
| 7,824,373 B2 | 11/2010 | Kim et al. | |
| 8,002,753 B2 | 8/2011 | Krumme et al. | |
| 2011/0282381 A1 | 11/2011 | Cronin et al. | |

FOREIGN PATENT DOCUMENTS

| | | |
|---|---|---|
| EP | 0348146 A1 | 12/1989 |
| EP | 1752174 A1 | 2/2007 |

OTHER PUBLICATIONS

PCT, International Search Report, May 21, 2013, International App. No. PCT/US2013/042099, 14 pages.

*Primary Examiner* — Rebecca E Eisenberg
(74) *Attorney, Agent, or Firm* — Shook Hardy & Bacon L.L.P.

(57) ABSTRACT

A self-contained apparatus and corresponding methods are provided for delivering viscous fluids in a controlled manner, such as delivering a viscous fluid in a surgical setting. The self-contained apparatus can include a motion following pressure regulator that allows for linear control of a regulated pressure. The regulated pressure can be used for dispensing a viscous fluid from a syringe that is coupled to the self-contained apparatus. The pressure regulator regulates a pressure derived from a pressurized fluid reservoir located at least partially within a housing of the apparatus. This allows the viscous fluid to be delivered using pressure to provide a driving force greater than a force easily delivered manually, while still allowing a surgeon to retain fine control over the rate of viscous fluid delivery.

20 Claims, 4 Drawing Sheets

VISCOUS FLUID INJECTOR

CROSS-REFERENCE TO RELATED APPLICATIONS

This application claims the benefit of U.S. Provisional Application 61/651,488, titled "Viscous Fluid Injector", which was filed on May 24, 2012, the entirety of which is incorporated herein by reference.

FIELD OF THE INVENTION

This invention is related to medical devices for the injection of fluids, such as viscous fluids, as well as methods for injecting fluids using such devices.

BACKGROUND

Vitreoretinal surgeries are conducted in an operating room under sterile conditions to prevent the risk of infection, particularly endophthalmitis; a rapid devastating infection that can cause blindness in a few days. The patient's eye is cleaned with an antiseptic, and then isolated with a sterile drape that fully covers the patient with only the eye exposed. A sterile field is established around the patient such that any personnel or instrumentation must be suitably scrubbed, draped or sterilized following standard aseptic procedures. A surgical microscope is used to view the interior of the eye through the patient's cornea and lens. The surgeon uses sterilized instruments including an infusion cannula to maintain intraocular pressure; an entry system to enable access to the posterior segment of the eye; a vitrectomy probe to cut and aspirate the vitreous gel; an illumination probe to provide light for visibility; various micro forceps and scissors for membrane manipulation and dissection; and specialized instruments as needed. Conventionally, the infusion, vitrectomy probe, illumination probe and aspiration are driven by a surgical console that sits outside the sterile field, and controlled by the surgeon using a multifunction foot pedal. Changes to the console settings are conducted by either a sterile scrub nurse assistant or circulating nurse that is outside of the sterile field.

Following a vitrectomy to repair a retinal tear and/or detachment, the surgeon may leave a tamponade in the eye to stabilize the retina during the healing process. If the detachment is localized and not severe, the tamponade can be a gas bubble of air or a mixture of air with an expansile gas ($SF_6$, $C_2F_6$, or $C_3F_8$). The bubble is absorbed over time from days or weeks depending on the gas and concentration used and no further surgery is required. For severe or chronic detachments, however, silicone oil is used and typically left in the eye for 3 to 12 months to allow the retina to reattach. Follow-on surgery is required to remove the oil. Typical oils are highly purified silicone (polydimethylsiloxane) in the viscosity range of 1000 to 5000 centistokes that are injected to fill the eye at the conclusion of vitreous surgery. The fluid volume required is typically 4-6 milliliters and can approach 10 milliliters or more in patients that are highly myopic (long eyes).

Due to the high viscosity of the fluid and the relatively small size of the incisions used for vitrectomy surgery, the injection of the silicone is performed using a pressurized syringe as it is difficult to manually generate the forces required to inject the viscous silicone oil through the small incision. Conventional methods are to use devices, such as those described U.S. Pat. No. 7,601,140 or U.S. Pat. No. 6,997,904, to attach to a syringe full of silicone oil to a high-pressure air source controlled by the surgical console. The surgeon modulates the silicone oil flow rate through the use of a foot pedal up to the maximum pressure setting on the console, which is typically supplied with hospital wall air or large nitrogen bottles. The surgeon will use the maximum pressure at the beginning of the fill cycle to induce the maximum flow rate to reduce the time it takes to fill the eye. As the eye fills, he will decrease the pressure so that he can reduce the flow rate to prevent overfilling and thus over pressurizing the eye. The ability to continuously modulate the flow rate is essential to the procedure.

Some of the difficulties with conventional methods for delivery of silicone oil arise from performing an injection within a sterile operating field using a device that is coupled to a required console located outside of the non-sterile field. As a result, two nurses are typically required to assist the surgeon with setting up or operating the device. A sterile scrub nurse connects the syringe filled with silicone oil to the pressure delivery device and carefully passes the tube set to a non-sterile circulating nurse ensuring that the sterile barrier is not compromised. The non-sterile circulating nurse connects the pressure delivery device tube set to the console and adjusts the maximum pressure settings. In addition to requiring multiple personnel, the requirement of having an additional connection (or connections) that must pass from the sterile field to outside of the sterile field is also undesirable. Also, the console devices used for providing pressure for the pressure delivery device are typically limited to providing a pressure available from a "house" gas source. This pressure limitation with the inherent pressure drop of the console pneumatic system, results in a maximum output pressure of only about 80 psig or less. As improvements in vitreous surgical instruments allow surgeries to move from the traditional 20 gauge to smaller 23, 25 and 27 gauge incisions, the limitation of having 80 psig (or less) pressure available means that longer injection times are required for such smaller incisions. These conventional methods for delivery of silicone oil are still in use today, in spite of decades of awareness of the difficulties and shortcomings associated with the conventional methods. Thus, there is a long-felt need within the art to provide an alternative to such conventional methods.

U.S. Pat. No. 8,002,753 describes a self-contained pressurized injection device. The device includes a volume of pressurized fluid, where the volume can be moved between a first position and a second position. In the second position, the pressurized fluid becomes available for providing pressure for pushing a medicament out of the injection device. The flow rate of a medicament out of the injection device can be controlled by constricting the size of the conduit for delivering the medicament.

SUMMARY

In an embodiment, an apparatus for injecting a fluid is provided. The apparatus includes a housing; a reservoir of pressurized fluid; a continuously variable pressure controller contained within the housing, the continuously variable pressure controller being in fluid communication with the reservoir of pressurized fluid when the reservoir is in an open state; an actuator mechanically coupled to the pressure controller, the mechanical coupling corresponding to a coupling for continuously varying a pressure regulated by the pressure controller; a housing coupler; and a housing sealing element. Preferably, the actuator is movable within a range along an axis of motion, the mechanical coupling of the actuator to the pressure controller providing a linear relationship between displacement of the actuator and a pressure regulated by the pressure controller for at least a portion of the range along the axis of motion.

In another embodiment, a method for injecting a viscous fluid is provided. The method includes opening a reservoir containing a pressurized fluid, the pressurized fluid having a first pressure; passing the pressurized fluid through at least one pressure regulation stage to produce pressurized fluid at a regulated pressure, the regulated pressure being lower than the first pressure; moving an actuator, the actuator being mechanically coupled to the at least one pressure regulation stage, along an axis of motion to control the regulated pressure, the regulated pressure being linearly and continuously dependent on an amount of movement of the actuator along the axis of motion for at least a portion of a range for the axis of motion; passing the pressurized fluid at the regulated pressure into a first volume of a dispensing device, the first volume being in fluid communication with a surface of a piston; and displacing the piston within the dispensing device to inject a viscous fluid contained in a second volume of the dispensing device.

This Summary is provided to introduce a selection of concepts in a simplified form that are further described below in the Detailed Description. This Summary is not intended to identify key features or essential features of the claimed subject matter, nor is it intended to be used as an aid, in isolation, in determining the scope of the claimed subject matter.

BRIEF DESCRIPTION OF THE DRAWINGS

The invention is described in detail below with reference to the attached drawing figures, wherein.

DETAILED DESCRIPTION

Overview

Figure 1A:
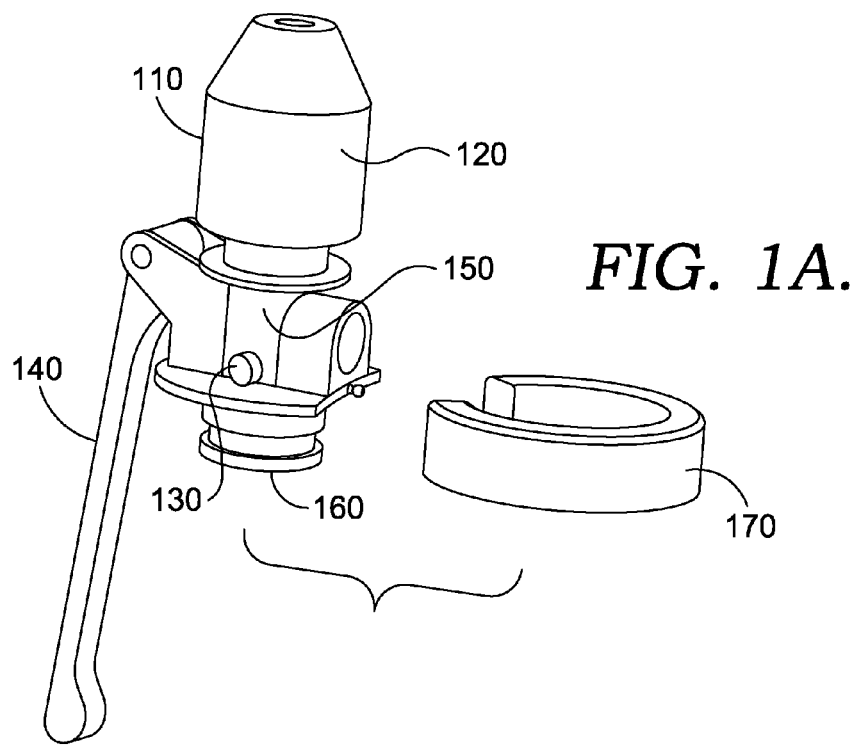
FIGS. 1A and 1B schematically show examples of an apparatus according to an embodiment of the invention.

In various embodiments, a self-contained apparatus and corresponding methods are provided for delivering viscous fluids in a controlled manner, such as delivering a viscous fluid in a surgical setting. The self-contained apparatus can include a motion following pressure regulator that allows for linear control of a regulated pressure. The regulated pressure can be used for dispensing a viscous fluid from a syringe that is coupled to the self-contained apparatus. The pressure regulator regulates a pressure derived from a pressurized fluid reservoir located at least partially within a housing of the apparatus. This allows the viscous fluid to be delivered using pressure to provide a driving force greater than a force easily delivered manually, while still allowing a surgeon to retain fine control over the rate of viscous fluid delivery. Preferably, the size of the pressurized fluid reservoir is such that the majority of the reservoir contents are expelled at the completion of the delivery of the viscous fluid and such that the self-contained apparatus can be configured as an ergonomic hand-held surgical instrument.

As one example, after some vitrectomy surgeries, a viscous fluid needs to be injected into the posterior segment of the eye. It is important to not over fill the posterior segment as excess viscous fluid can damage the function of the anterior anatomies of the eye and result in cataracts, corneal keratopathy, pupillary block glaucoma, and other disorders of the anterior segment. Additionally, the eye represents a fixed volume enclosed organ. Due to the nature of the eye, the organ is relatively pressure sensitive. As a result, a careful pressure balance needs to be achieved when injecting a viscous fluid into the posterior segment of the eye. Sufficient viscous fluid needs to be injected such that the retina will reattach after surgery. However, over-filling needs to be avoided so that the eye is not damaged due to internal pressure increases caused by excess viscous fluid. Having accurate control of the rate of delivery of the viscous fluid is valuable for the surgeon to achieve this balance of factors.

The self-contained pressurized delivery apparatus described herein overcomes various long-felt problems with existing systems and methods for delivery of viscous fluids in surgical settings. Many conventional methods for delivering viscous fluids require connecting a syringe or other delivery device to a console located outside of the sterile field for a surgery. By contrast, the self-contained apparatus of the claimed invention does not require an external connection in order to provide pressure for injecting a fluid. Instead, it operates untethered with the pressure fluid reservoir located within (or at least partially within) a housing of the apparatus. Additionally, the apparatus according to the invention allows for initiation of fluid delivery and linear control of the delivery rate using a single actuator that can be readily activated using one hand. This can help to minimize the setup time of the scrub nurse, eliminate the need for the circulating nurse, and reduce apparatus interaction required by the surgeon in order to operate the device while enhancing the control the surgeon has over the delivery rate of the viscous fluid. Additionally, by controlling the pressure used for fluid delivery, as opposed to attempting to directly control the flow rate by modifying the restriction of the fluid flow path, the apparatus allows for linear control over the rate of fluid delivery. This is in contrast to methods of flow control involving modification of the flow path restriction, which involve an exponential dependence of the flow rate on the radius of the flow path ($r^4$).

Apparatus for Pressure-Regulated Delivery of Viscous Fluids Via Syringe

In various embodiments, an apparatus for pressure-regulated delivery of a viscous fluid via a syringe (or other fluid delivery device) can include at least a housing for the apparatus, a reservoir of pressurized fluid, a pressure controller or regulator, and an actuator for controlling the regulated pressure achieved by the pressure regulator. Examples of an actuator can include a lever arm, a push button, and/or other structures that allow for a linear relationship between the position of an actuator and a regulated pressure.

The housing for the self-contained apparatus provides a convenient shell for maintaining the physical relationship between the pressurized fluid reservoir, the pressure regulator, and the actuator for controlling the pressure regulator. Optionally, the housing can have multiple pieces that are removably attached. For example, the housing can include a housing cap that is threaded to allow the cap to be screwed onto a corresponding housing body. As another example, the portion of the housing that couples the housing to a syringe can optionally include a removable portion.

One structure contained (at least partially) within the housing can be a pressurized fluid reservoir. The pressurized fluid reservoir can correspond to a volume contained within the housing, or a vessel defining a separate volume within the housing can be used as the pressurized fluid reservoir. In either situation, the pressurized fluid reservoir can initially be in a sealed state, so that pressurized fluid within the reservoir is not in fluid communication with the pressure regulator. The reservoir can correspond to any convenient size that is suitable for use in a self-contained (such as hand-held) apparatus. For example, the reservoir can have a reservoir volume of at least about 0.5 ml, such as at least about 1.0 ml. Additionally or alternatively, the reservoir volume can be less than about 10.0 ml, such as less than about 5.0 ml.

In some preferred embodiments, the pressurized fluid reservoir can remain in a sealed or closed state until after a syringe is coupled to the housing. Options for converting the pressurized fluid reservoir from a closed state to an open state can include, but are not limited to, puncturing a wall of the reservoir and/or opening a valve associated with the reservoir. For example, a pin within the housing can be mechanically coupled to the actuator, so that movement of the actuator from an initial position results in displacement of the pin toward a wall of the reservoir. Movement of the actuator by a sufficient amount can result in the pin piercing the reservoir wall, thus enabling fluid communication between the reservoir and the pressure regulator. Alternatively, the piercing pin can be displaced using an actuator that is different from the actuator for controlling the pressure controller. Still another option is to use a stationary pin that is part of the housing. The reservoir can then be displaced toward the pin as the top of the housing is coupled to the body of the housing. In yet another option, the piercing pin can be replaced with a valve opening pin where movement of the pin and/or the reservoir relative to each other opens a valve associated with the reservoir. For example, the reservoir can include a valve that is initially in a closed state. A valve opening pin can then be used to convert the valve to an open state, such as by having the pin move a lever, arm, or other structure that changes the valve from a closed to an open (or at least partially open) state.

After opening of the reservoir, the pressure controller can regulate the amount of pressure delivered to an attached or coupled delivery device. In a default or initial state, the pressure regulator can be closed, so that no pressurized fluid is allowed to pass through the regulator to a coupled syringe. Using the actuator, a fluid pathway within the pressure controller can be opened to allow a regulated amount of pressure to be delivered to a coupled syringe or other delivery device. The regulated pressure level can be substantially below the pressure of pressurized fluid delivered by the reservoir. For example, the pressure of the pressurized fluid leaving the reservoir can be at least about 250 psig, such as at least about 500 psig, and preferably at least about 750 psig or at least about 900 psig. The pressure regulator can regulate the pressure delivered to the coupled syringe, so that the delivered pressure is from about 70 psig to about 150 psig. For example, the delivered pressure can be at least about 70 psig, or at least about 80 psig, or at least about 90 psig. Additionally or alternately, the delivered pressure can be about 150 psig or less, such as about 125 psig or less, or about 100 psig or less. In some alternative embodiments, the delivered pressure can be below and/or above the ranges noted above, depending on the viscosity of the desired viscous fluid for injection and the desired rate of injection.

The pressurized fluid within the reservoir can be any convenient fluid for achieving a desired pressure upstream from the pressure regulator. Examples of suitable fluids can be air, nitrogen, carbon dioxide, an (aerosol) propellant, or any other convenient fluid for providing a desired pressure. In some aspects, a two-phase source can be beneficial. For example, carbon dioxide has a liquid (condensed) phase that is achievable under conditions that can be maintained in a closed reservoir. When the reservoir is opened, a condensed phase within the reservoir can provide a relatively constant pressure upstream from the pressure regulator. Other two phase (or multi-phase) systems can be used as the "fluid" inside the reservoir. It is noted that even if the material within the reservoir is actually a solid prior to opening the reservoir, the reservoir is still defined herein as corresponding to a fluid reservoir, as a gas phase will still be delivered to the pressure regulator.

Preferably, the pressure controller can be a motion-following pressure regulator. This allows the pressure delivered to the coupled syringe by the pressure regulator to be controlled by use of a mechanical actuator that is mechanically coupled to the pressure regulator, such as a lever or other convenient structure. The initial state of the actuator can correspond to the initial state of the pressure regulator, so that no pressure is delivered to a coupled syringe when the actuator is not activated. Movement of the actuator along the axis of motion can then be used to change the pressure regulator from an initial state to a state where pressurized fluid is allowed to pass through the pressure regulator, which enables delivery of pressure to the coupled syringe. As an example of an axis of motion, if the actuator corresponds to a lever arm, the axis of motion for the lever arm can correspond to a radial path around a pivot point. If the actuator corresponds to a push button, the axis of motion can be a linear path.

The actuator can enable changes in the delivered pressure in a continuous manner. Preferably, the pressure delivered by the pressure regulator can have a linear correlation with the motion of the actuator through at least part of the range of motion of the actuator. For example, a first amount of movement of the actuator to reach a first actuator position may be needed to trigger any fluid flow through the regulator. After the first amount of movement to reach the first position, the pressure delivered via the pressure regulator can vary in a linear manner with the movement of the actuator until a second actuator position is reached. After the second position, the maximum delivered pressure has been achieved, so that further movement of the actuator along the range of motion does not further modify the pressure. In other embodiments, any movement of the actuator from the initial position can result in enabling flow through the pressure regulator. In still other embodiments, the pressure delivered by the pressure regulator can vary with movement of the actuator until the actuator reaches the limit of possible movement along the axis of motion for the actuator. In yet other embodiments, the linear relationship of the movement of the actuator with the delivered pressure can be maintained over only a portion of the full range of motion of the actuator along the axis of motion. The pressure controller can be a single stage pressure regulator or a multi-stage pressure regulator.

After movement of the actuator to enable fluid flow through the pressure regulator, the pressurized fluid will pass through the pressure regulator until the pressure corresponding to the pressure regulator position (and the corresponding actuator position) is achieved. At that point, additional flow of pressurized fluid will occur based on any displacement of the syringe dispensing piston and/or due to any movement of the actuator to select a higher pressure. Otherwise, additional pressurized fluid will not flow through the pressure regulator once the regulated pressure is achieved.

At various times, it can be desirable to vent the pressure within the region between the pressure regulator and the syringe piston or plunger. The housing can further include a relief valve to allow for release of pressure within this region. The relief valve can allow overpressure within the housing to be released, or the valve can optionally be triggered manually to vent pressure. For example, the relief valve can open when the actuator is returned to the initial position, so that the pressure delivered by the pressure regulator is not maintained unless the actuator is displaced at least partially along the axis of motion. Preferably, the relief valve can include a filter, so that pressurized gas that exits through the relief valve is filtered prior to entering the sterile field of the surgical area. Optionally, the housing can further include a secondary relief valve, optionally associated with a secondary actuator, to allow for release of pressure within the housing to provide an alternative pathway for relieving pressure within the housing.

One option for providing a linear relationship between the position of the actuator along an axis of motion and the pressure delivered to a syringe is to use springs to control the opening and closing of one or more valves for allowing fluid flow. Based on Hooke's law, the amount of force exerted by a spring has (approximately) a linearly relationship to the amount of compression or extension of the spring from a rest position. Using a valve that is opened or closed based on a balancing a pressure force against a spring force can enable a linear control method for pressure regulation. In this description, references to a linear relationship between the position of an actuator and a pressure delivered to a syringe are defined to include relationships where small amounts of non-linearity can occur, such as small amounts of non-linearity due to the behavior of an actual spring (in the normal displacement range of the spring) being different from the idealized behavior represented by Hooke's law.

As an example, the flow channel for transferring fluid from the high pressure reservoir to the syringe can include a ball valve. A first bias spring can be used to hold the ball in a valve seat when the actuator is in the initial position. When an actuator is moved along an axis of motion, the actuator can displace an assembly that includes a second spring and a protrusion (such as a poppet) that can force the ball away from the valve seat. When the protrusion forces the ball away from the valve seat, this results in compression of the first bias spring The second spring can have a higher stiffness value or spring constant than the first bias spring, so that movement of the actuator primarily results in compression of the first bias spring rather than the second spring.

Displacement of the second spring forces the ball away from the valve seat, which allows fluid to flow. This results in increasing pressure in the volume downstream from the ball valve. The second spring can be part of an assembly that includes a surface that is exposed to the pressure downstream from the ball valve. As the pressure in the volume downstream from the ball valve increases, this pressure applies a force against the surface of the assembly. This compresses the second spring, which at least partially returns the protrusion toward the original position and therefore reduces the displacement of the ball from the valve seat. When the pressure downstream from the ball valve is sufficient, the second spring will be compressed to the point where the ball returns to the valve seat and closes the valve. The amount of compression required to close the ball valve will be dependent on the amount of initial displacement of the ball using the actuator. Thus, increasing the pressure downstream from the ball valve can be controlled in a linear manner.

In this type of example, when the actuator is moved back toward the initial position, a flow path can be opened to allow for a decrease in pressure that is proportional to the location of the actuator. For example, when the actuator is used to increase the pressure, the ball of the ball valve can be displaced by a protrusion corresponding to a poppet. The poppet can move in a small channel between the second spring assembly and the ball valve. Depending on the pressure within the volume downstream of the ball valve and the position of the actuator, the poppet can allow for fluid flow through the ball valve, fluid flow through a flow channel at the opposite end of the poppet, or both the ball valve and the flow channel can be closed to maintain the current pressure. When the poppet is under load to keep the ball valve open, a portion of the poppet can be in contact with the second spring assembly and seated in a flow pathway for pressure reduction. The poppet can then seal the flow pathway for pressure reduction when the poppet is under load. When the actuator is moved back toward the initial position, the poppet is not forced to be seated in the flow pathway, allowing pressure to be released. When sufficient pressure is released, the amount of displacement of the second spring is reduced, which causes the poppet to become seated in the flow path again.

Alternatively, a second release (ball) valve can be controlled by the actuator to allow for linear decrease of pressure. A similar type of arrangement can be used, so that a pressure differential across the release valve compresses a spring to open the valve. Displacement of the actuator can force the ball of the release valve back toward the valve seat to close the release valve, so that a pressure differential across the valve can be maintained.

A coupling structure can be used to allow the housing to be attached to a viscous fluid delivery device, such as a syringe. Many types of syringes are currently available, with a variety of standard sizes for the proximate end of the syringe and a variety of standard sizes for the distal end. In this discussion, a proximate end of a syringe refers to the part of a syringe that is closest to a user, while the distal end of a syringe refers to the end that is closest to the recipient of an injection (i.e., the needle end or other injection end). The housing can provide a coupling for a syringe that matches one of the standard sizes for the proximate end of the syringe. Any convenient structure for securely coupling the syringe to the housing can be used.

As an example, the coupling structure can correspond to a structure that can be removed from the apparatus. The coupling structure can be made of a flexible material (such as a flexible silicone or other rubberized material) that can be deformed to allow the coupling structure to be placed around an interface between the syringe and the housing. The coupling structure can include at least two grooves or other indentations for receiving lips or flanges of the housing and syringe to assist in securing the syringe to the housing. For example, a first groove of the coupling structure can receive a lip of the housing while a second groove of the coupling structure receives a lip of the syringe.

In another embodiment, the coupling structure can be an integral part of the housing. Generally, the coupling structure can be suitable for mechanically joining the injector with the syringe so that the housing and the syringe will not separate at the desired operating pressure. Preferably, the coupling structure can provide a seal to avoid leaks at the desired operating pressure. Preferably, the coupling structure can distribute stress on a coupled syringe so that the syringe structure will remain stable (not break) at the desired operating pressure, such as remaining stable at twice the desired operating pressure.

The housing can also including a sealing structure for providing a seal between the interior of the syringe and the housing. The sealing structure can correspond to a plug, gasket, or another type of structure with an outer diameter that is similar to the expected inner diameter of the syringe (or other delivery device). The plug or gasket structure can provide a sufficiently tight fit between the housing and the syringe so that pressure is not lost due to fluid escaping between the inner wall of the syringe and the outer surface of the plug or gasket. During operation of the pressure-delivery apparatus, an interior channel in the plug or gasket can allow for delivery (fluid communication) of pressurized gas from the pressure regulator in the housing into the inner volume of the syringe. The sealing structure can be shaped to also be in contact with a top surface of the wall of the syringe, or a separate gasket-type structure can be used to form a seal between the top of the syringe and the housing.

Preferably, a syringe can be provided that is pre-loaded with a suitable amount of a viscous fluid. For some applications, the viscous fluid can correspond to a silicone oil, such as polydimethoxysilane (PDMS), with a viscosity of about 1000 to about 5000 cSt at 25° C. In other applications, the viscous fluid can correspond to a silicone oil, a perfluorocarbon liquid, a viscoelastic fluid, a dental adhesive, or another fluid with a viscosity of at least about 500 cSt at 25° C.

Example of Apparatus Configuration

Figure 1B:
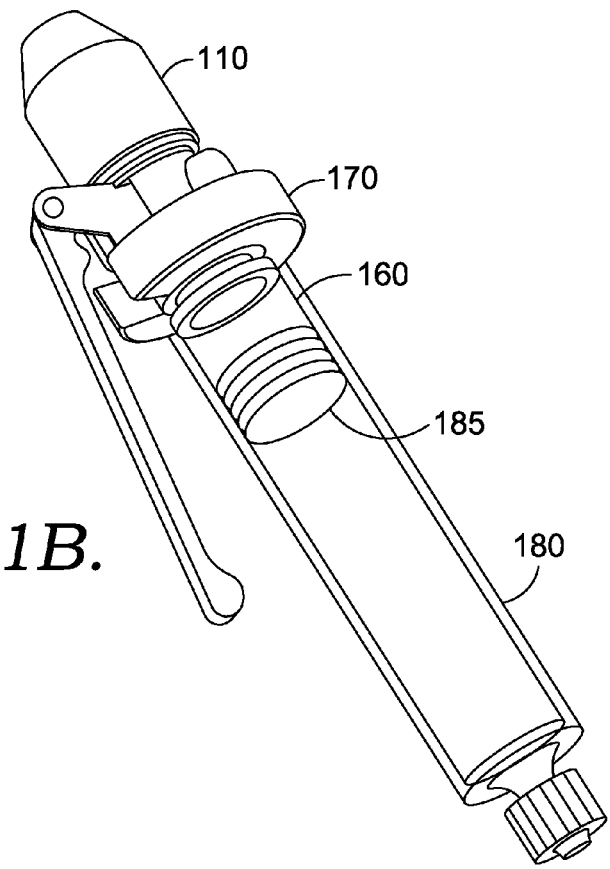

FIG. 1A shows an exterior overview of a pressure-delivery apparatus according to an embodiment of the invention. In FIG. 1A, the apparatus includes a housing 110 that contains a pressurized gas source 120, such as a reservoir of pressurized liquid/gas, and a pressure controller or regulator 150. The housing also includes a relief valve 130. An actuator 140 is mechanically coupled to the housing 110 to define an axis of motion for the actuator. The actuator 140 is also mechanically coupled to the pressure controller to allow for regulation of a pressure. The housing further comprises a syringe seal 160 and an optionally detachable syringe coupler 170. The syringe seal 160 and optionally detachable syringe coupler 170 allow a syringe (or another delivery device) to be attached to housing 110 in a manner that allows for pressurization of the volume in a syringe above the piston or plunger for dispensing a viscous fluid. FIG. 1B shows an example of the housing 110 after coupling of a syringe 180 to the housing by using syringe coupler 170 and/or syringe seal 160. The volume 182 in the syringe above the syringe piston 185 is in fluid communication with the downstream side of pressure controller 150. When pressurized fluid is passed through pressure controller 150 to create a pressure greater than ambient on the downstream side of the pressure controller 150, the piston 185 can be displaced toward the distal end of syringe 180 due to the force exerted on piston 185.

Figure 2:
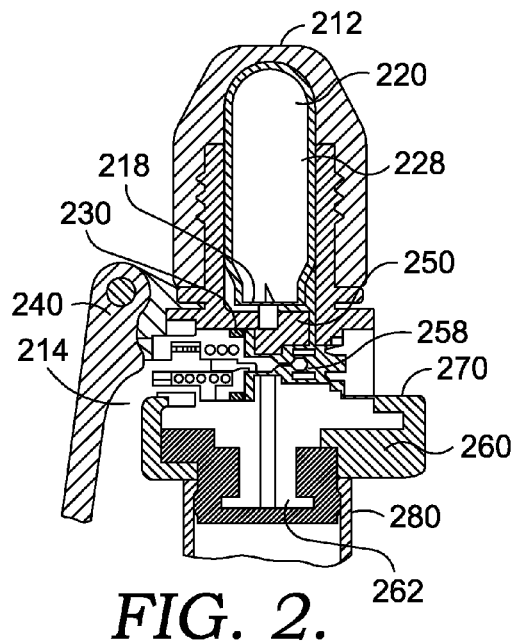
FIG. 2 shows a cross sectional view of an apparatus according to an embodiment of the invention.

FIG. 2 shows a cross section of an apparatus according to an embodiment of the invention. In the embodiment shown in FIG. 2, the housing comprises a housing cap 212 that is threaded, so that housing cap 212 can be rotated to tighten the housing cap down against the housing body 214. This imposes a force on the vessel against the puncture pin 324, eventually puncturing the vessel and releasing the gas pressure. Alternatively, the pin 324 can be a valve opening pin that mechanically acts on a valve (not shown) to convert the valve from a closed to an open state.

In the embodiment shown in FIG. 2, housing body 214 contains a pressure controller 250. The housing body also includes a vent or relief valve 230. The actuator 240 for controlling the pressure controller 250 is coupled to the housing body 214. A syringe coupler 270 and a syringe seal 260 allow the housing body 214 to be coupled to a syringe 280 in a sufficient manner to allow an above-ambient pressure to be supported within the syringe.

In the embodiment shown in FIG. 2, the housing cap 212 defines a space around vessel 220 that is at an ambient pressure 218. The vessel 220 contains a fluid (possibly including a source for generating a fluid) that is at an elevated pressure 228 relative to ambient. The fluid in vessel 220 can be referred to as being upstream from the pressure controller 250. After vessel 220 is opened, the pressure controller 250 is exposed to this elevated pressure. When actuator 240 is used to enable fluid flow through the pressure controller 250, a regulated pressure 258 that is less than elevated pressure 228 is achieved downstream from pressure controller 250. The regulated pressure 258 is also present in a volume in syringe 280, due to fluid flow of the pressurized fluid (at the regulated pressure 258) through conduit 262 that passes through seal 260.

Figure 3A:
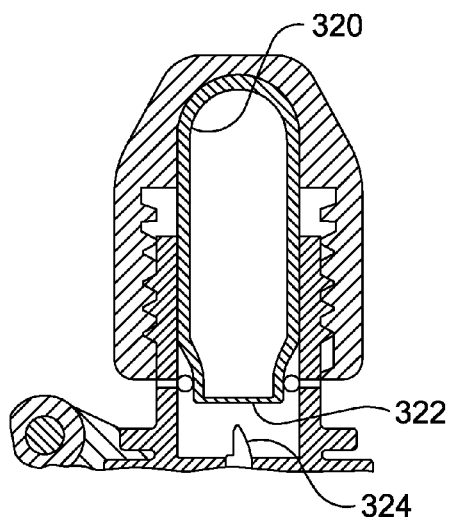
FIGS. 3A and 3B show cross sectional views of an apparatus according to an embodiment of the invention.
Figure 3B:
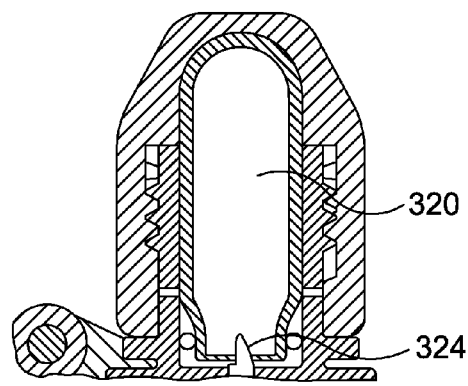

In an embodiment shown in FIGS. 3A and 3B, a vessel or other reservoir 320 is depicted in a closed state (FIG. 3A) and in an open state after piercing of a wall of the reservoir 320 (FIG. 3B) by a pin or other puncture device 324. FIG. 3A shows the reservoir 320 while the reservoir is in a closed state. In FIG. 3A, the pin 324 is below the level of a lower wall 322 of reservoir 320. This represents an initial closed state of the reservoir prior to use. As the housing cap is screwed down on to the housing body, the reservoir 320 is displaced toward the pin 324. This eventually results in pin 324 piercing wall 322 of reservoir 320, which allows fluid communication between the pressurized interior of the reservoir 320 and the pressure regulator.

Figure 4:
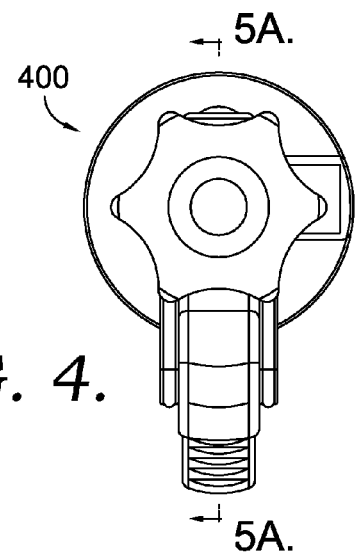
FIG. 4 shows a top view of an apparatus according to an embodiment of the invention.

FIGS. 4 and 5A-5D schematically show a detailed view of a pressure-delivery apparatus according to another embodiment of the invention. FIG. 4 provides a top-down view of an apparatus 400.

Figure 5A:
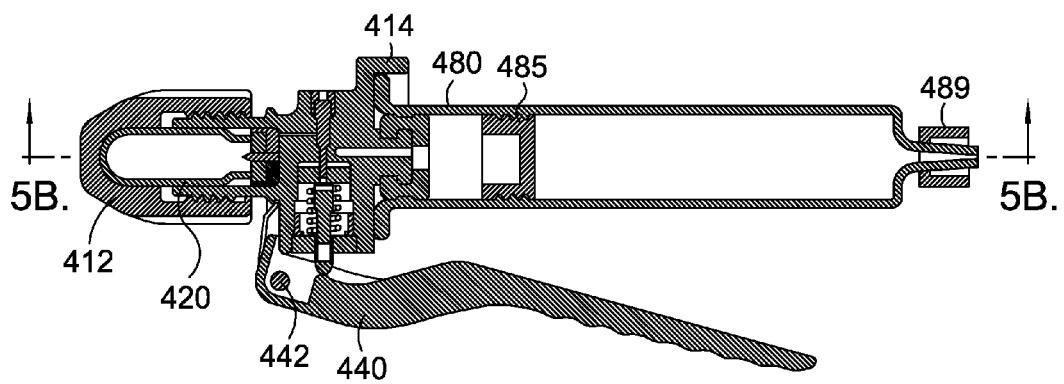
FIGS. 5A-5D show internal views of an apparatus according to embodiments of the invention.

FIG. 5A shows a cross section of the apparatus along the cross-sectional line "A" shown in FIG. 4. In FIG. 5A, the apparatus includes a housing cap 412 and a housing body 414. Housing cap 412 is shown as being threaded for attachment to housing body 414. A gas canister 420 provides a vessel for holding a pressurized fluid (optionally including a pressurized compound in a condensed phase that acts as a source for the pressurized fluid). The gas canister is contained within the housing formed by the combination of housing cap 412 and housing body 414. The apparatus further includes an actuator 440 in the form of a lever or trigger arm. The axis of motion for the actuator is defined by pivot location 442. In FIG. 5A, the apparatus is shown coupled to a syringe 480. Syringe 480 includes a piston 485 that can be displaced to expel a viscous fluid out through the distal end of the syringe. A connector such as a Luer lock connector 489 can allow a needle to be coupled to the bottom of the syringe 480. A portion of FIG. 5A is explained in more detail below.

Figure 5B:
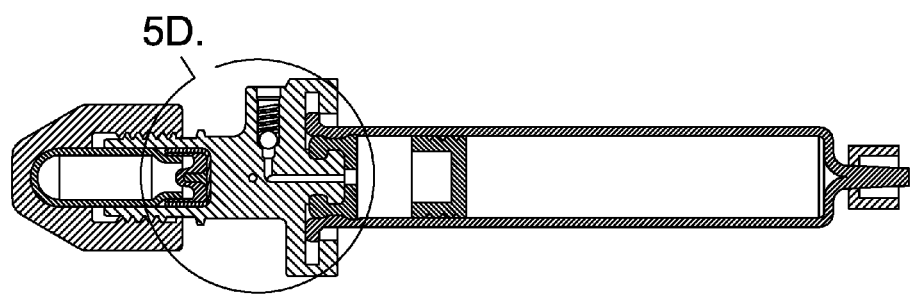

FIG. 5B shows a cross section of the apparatus along the cross sectional line "B" shown in FIG. 5A. FIG. 5B shows a region D that is explained in more detail below.

Figure 5C:
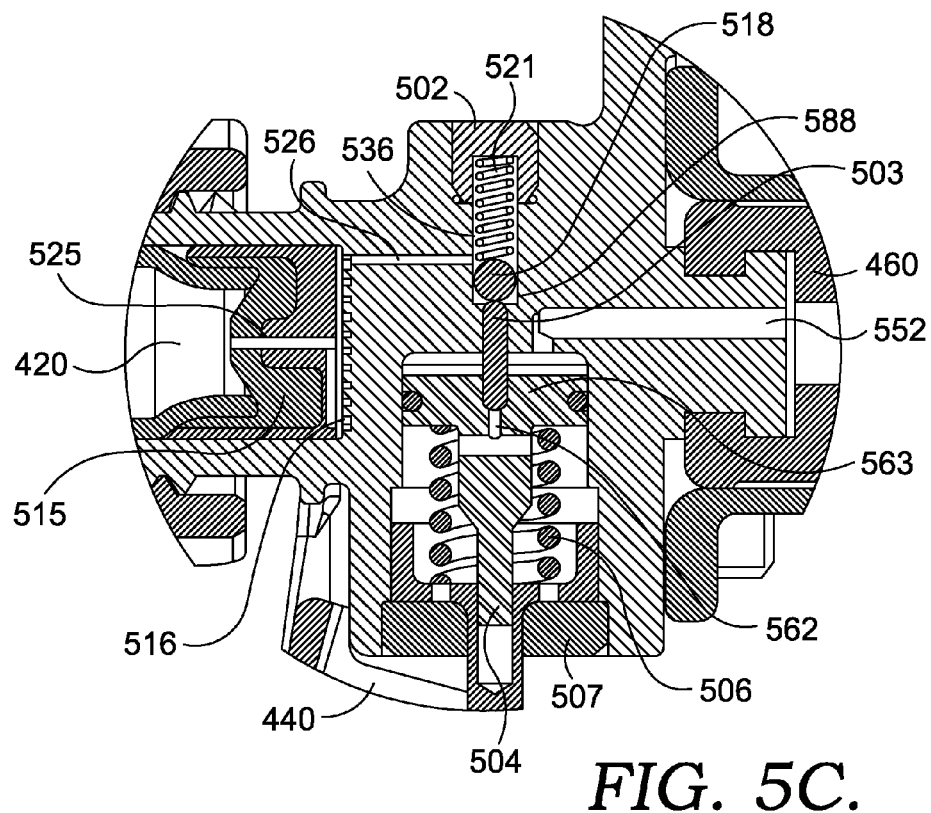

FIG. 5C shows an expanded view of the pressure controller or regulator shown in FIG. 5A. In FIG. 5C, additional details are provided regarding a pressure controller or regulator according to an embodiment of the invention. In FIG. 5C, actuator 440 is mechanically coupled to piston 504. Side cap 507 can be removed to allow for assembly of piston 504 and a piston regulator spring 506 during assembly of the pressure regulator. When actuator 440 is moved from its initial position, the actuator impinges on piston 504, causing piston 504 and poppet 503 to be displaced toward ball 518. When poppet 503 contacts ball 518, ball 518 is displaced from ball seat interface or seal 588. This opens a flow path to allow fluid communication between the upstream side of the pressure regulator to the downstream side of the pressure regulator. When the actuator 440 is in the initial state, a spring 521 biases the ball toward ball seat interface or seal 588, so that flow is not enabled. During assembly of the pressure regulator, high pressure cap 502 can be removed, so that poppet 503 and ball 518 can be inserted into chamber 536. High pressure cap 502 also pre-loads spring 521 against ball 518.

During operation, after reservoir 420 is opened, pressurized gas passes through conduit 525 in filter cover 515 to reach filter 516. The piercing pin for opening the reservoir 420 is also contained in conduit 525. Filter 516 can be, for example, a 0.2 μm filter so that any gas that might escape into the sterile field is a filtered gas. After passing through filter 516, the gas passes through channel 526 to reach the chamber 536 that contains the ball 518 and the bias spring 521. Movement of ball 518 away from the ball seat allows gas to pass through conduit 552 and into a coupled syringe (not shown) through syringe seal 460.

As gas passes through conduit 552, the pressure on the downstream side of the ball valve will increase. The increasing pressure exerts a force on the surface 563, resulting in compression of piston regulator spring 506. Increasing the compression of piston regulator spring 506 will result of displacement of poppet 503 away from ball 518 until ball 518 becomes seated again in interface 588.

When the actuator 440 is moved toward the initial position, the poppet 503 may become unseated from the bottom of conduit 562. This can occur if the actuator is returned to the initial position, or if the pressure on surface 563 is sufficient so that the distance between ball 518 and the bottom of conduit 552 is greater than the length of the poppet. When poppet 503 becomes unseated, fluid can flow through conduit 562 to allow for reduction of pressure downstream from the ball valve.

By using a pressure regulator as shown in FIG. 5C, the amount of pressure that a syringe piston is exposed to can be controlled using an actuator for the apparatus. Based on a design similar to the design shown in FIGS. 5A-5C, the actuator can be used to provide linear control of the regulated pressure that is delivered into the syringe, and therefore linear control over the rate of delivery of a viscous fluid. This is in contrast to methods where an excess of pressure is provided for driving the piston in a syringe, and the flow rate is instead controlled by constricting a flow channel for the fluid being injected.

Figure 5D:
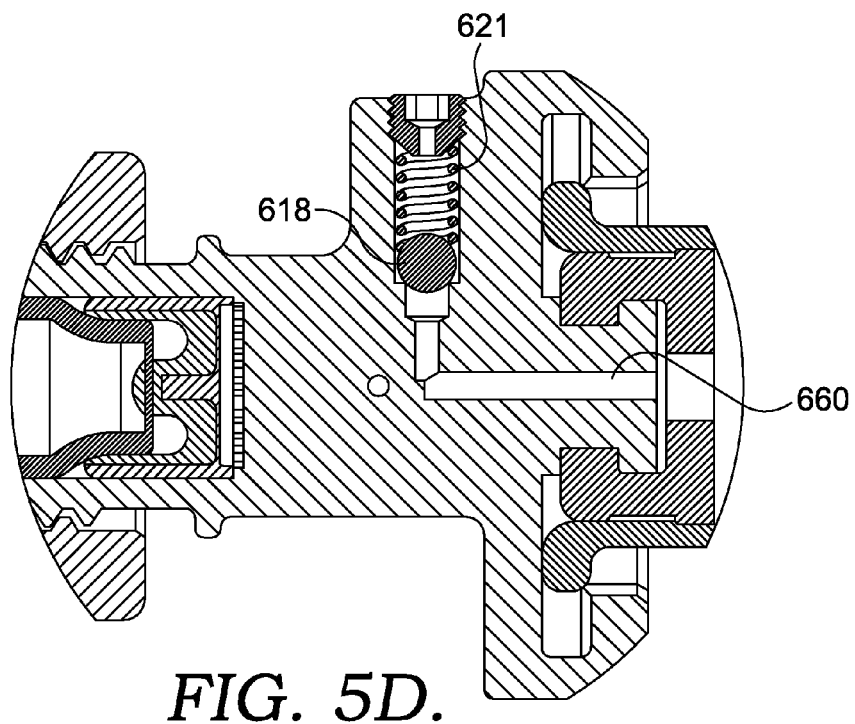

FIG. 5D shows a separate pressure relief valve to allow for release of pressure in the event that excess pressure is formed within the syringe and/or in the event that a separate method of venting pressure is desired. Ball 618 of the ball valve is biased toward a closed position by spring 621. Spring 621 can be manually compressed to allow for venting of pressure within the housing. Additionally or alternately, if a sufficient pressure is present within conduit 660, the ball 618 can be displaced to allow venting of the pressure.

ADDITIONAL EMBODIMENTS

Embodiment 1

An apparatus for injecting a fluid, comprising a housing; a reservoir of pressurized fluid; a continuously variable pressure controller contained within the housing, the continuously variable pressure controller being in fluid communication with the reservoir of pressurized fluid when the reservoir is in an open state; an actuator mechanically coupled to the pressure controller, the mechanical coupling corresponding to a coupling for continuously varying a pressure regulated by the pressure controller; a housing coupler; and a housing sealing element.

Embodiment 2

The apparatus of Embodiment 1, wherein the housing comprises a housing cap and a housing body.

Embodiment 3

The apparatus of Embodiment 2, wherein a rotation of the housing cap relative to the housing body creates a pathway for the fluid communication between the reservoir and the continuously variable pressure controller.

Embodiment 4

The apparatus of any one of the above embodiments, wherein the reservoir comprises at least one of a separated volume within the housing or a vessel at least partially contained within the housing.

Embodiment 5

The apparatus of any one of the above embodiments, further comprising a pin, the pin being adapted for at least one of converting the reservoir from a closed state to an open state by piercing a wall of the reservoir or converting a valve from a closed state to an open state.

Embodiment 6

The apparatus of any one of the above embodiments, wherein the pressure controller is a motion following pressure controller, a multi-stage pressure controller, or a combination thereof.

Embodiment 7

The apparatus of any one of the above embodiments, wherein the actuator is movable within a range along an axis of motion, the mechanical coupling of the actuator to the pressure controller providing a linear relationship between displacement of the actuator and a pressure regulated by the pressure controller for at least a portion of the range along the axis of motion.

Embodiment 8

The apparatus of any one of the above embodiments, wherein the actuator is at least one of a lever or a push button.

Embodiment 9

The apparatus of any one of the above embodiments, wherein providing a linear relationship between displacement of the actuator and a pressure regulated by the pressure controller comprises providing a linear relationship between displacement of the actuator toward an initial position for at least a portion of the range along the axis of motion and a decrease in the pressure regulated by the pressure controller.

Embodiment 10

The apparatus of any of Embodiments 1-6, wherein the actuator is movable within a range along an axis of motion, the mechanical coupling of the actuator to the pressure controller providing a linear relationship between displacement of the actuator and a pressure regulated by the pressure controller for at least a portion of the range along the axis of motion, the actuator optionally being at least one of a lever or a push button, the provided linear relationship between displacement of the actuator and a pressure regulated by the pressure controller preferably comprising a linear relationship between displacement of the actuator toward an initial position for at least a portion of the range along the axis of motion and a decrease in the pressure regulated by the pressure controller.

Embodiment 11

The apparatus of any one of the above embodiments, wherein a pressure regulated by the pressure controller is correlated with motion of the actuator between a first position and a second position along an axis of motion, the first position being different from an initial position of the actuator.

Embodiment 12

The apparatus of any one of the above embodiments, the housing further comprising a filter in a fluid communication path between the reservoir and the pressure controller.

Embodiment 13

The apparatus of any one of the above embodiments, further comprising a syringe coupled to the housing with the housing coupler.

Embodiment 14

The apparatus of any one of the above embodiments, wherein the housing coupler is removably attached to the housing.

Embodiment 15

The apparatus of any one of the above embodiments, wherein the pressurized fluid within the reservoir comprises a condensed phase and gas phase.

Embodiment 16

The apparatus of any one of the above embodiments, wherein the actuator is mechanically coupled to the housing, the mechanical coupling of the actuator to the housing providing a flow path for release of pressurized gas that is downstream from the pressure controller when the actuator is in an initial state.

Embodiment 17

A method for injecting a viscous fluid using the apparatus of any one of Embodiments 1-16.

Embodiment 18

A method for injecting a viscous fluid, comprising: opening a reservoir containing a pressurized fluid, the pressurized fluid having a first pressure, the pressurized fluid optionally comprising at least a condensed phase and a gas phase; passing the pressurized fluid through at least one pressure regulation stage to produce pressurized fluid at a regulated pressure, the regulated pressure being lower than the first pressure; moving an actuator, the actuator being mechanically coupled to the at least one pressure regulation stage, along an axis of motion to control the regulated pressure, the regulated pressure being linearly and continuously dependent on an amount of movement of the actuator along the axis of motion for at least a portion of a range for the axis of motion; passing the pressurized fluid at the regulated pressure into a first volume of a dispensing device, the first volume being in fluid communication with a surface of a piston; and displacing the piston within the dispensing device to inject a viscous fluid contained in a second volume of the dispensing device.

Embodiment 19

The method of Embodiment 18, further comprising: coupling the dispensing device to a housing, the reservoir of pressurized fluid being at least partially contained within the housing, the dispensing device being coupled to the housing prior to opening the reservoir of pressurized fluid.

Embodiment 20

The method of Embodiment 18 or 19, wherein opening a reservoir containing a pressurized fluid comprises at least one of piercing a wall of the reservoir or opening a valve associated with the reservoir.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

What is claimed is:

1. An apparatus for injecting a fluid, comprising
   a housing;
   a reservoir of pressurized fluid;
   a continuously variable pressure controller contained within the housing, the continuously variable pressure controller being in fluid communication with the reservoir of pressurized fluid when the reservoir is in an open state;
   an actuator mechanically coupled to the pressure controller, the actuator being movable within a range along an axis of motion, the mechanical coupling corresponding to a coupling for a) continuously varying a pressure regulated by the pressure controller, based on displacement of the actuator within at least a portion of the range along the axis of motion, for increases in the pressure regulated by the pressure controller and b) continuously varying the pressure regulated by the pressure controller, based on displacement of the actuator within at least a portion of the range along the axis of motion, for decreases in the pressure regulated by the pressure controller;
   a housing coupler; and
   a housing sealing element.

2. The apparatus of claim 1, wherein the housing comprises a housing cap and a housing body.

3. The apparatus of claim 2, wherein a rotation of the housing cap relative to the housing body creates a pathway for the fluid communication between the reservoir and the continuously variable pressure controller.

4. The apparatus of claim 1, wherein the reservoir comprises a vessel, the vessel being at least partially contained within the housing.

5. The apparatus of claim 1, wherein the reservoir comprises a separated volume within the housing.

6. The apparatus of claim 1, further comprising a pin, the pin being adapted for at least one of converting the reservoir from a closed state to an open state by piercing a wall of the reservoir or converting a valve from a closed state to an open state.

7. The apparatus of claim 1, wherein the pressure controller is a motion following pressure controller, a multi-stage pressure controller, or a combination thereof.

8. The apparatus of claim 1, wherein the mechanical coupling of the actuator to the pressure controller provides a linear relationship between displacement of the actuator and a pressure regulated by the pressure controller for at least a portion of the range along the axis of motion.

9. The apparatus of claim 8, wherein providing a linear relationship between displacement of the actuator and a pressure regulated by the pressure controller comprises providing a linear relationship between displacement of the actuator toward an initial position for at least a portion of the range along the axis of motion and a decrease in the pressure regulated by the pressure controller.

10. The apparatus of claim 1, wherein the actuator comprises at least one of a lever or a push button.

11. The apparatus of claim 1, wherein a pressure regulated by the pressure controller is correlated with motion of the actuator between a first position and a second position along an axis of motion, the first position being different from an initial position of the actuator.

12. The apparatus of claim 1, the housing further comprising a filter in a fluid communication path between the reservoir and the pressure controller.

13. The apparatus of claim 1, further comprising a syringe coupled to the housing with the housing coupler, the housing coupler optionally being removably attached to the housing.

14. The apparatus of claim 1, wherein the housing coupler is removably attached to the housing.

15. The apparatus of claim 1, wherein the pressurized fluid within the reservoir comprises a condensed phase and gas phase.

16. The apparatus of claim 1, wherein the actuator is mechanically coupled to the housing, the mechanical coupling of the actuator to the housing providing a flow path for release of pressurized gas that is downstream from the pressure controller when the actuator is in an initial state.

17. A method for injecting a viscous fluid, comprising:
opening a reservoir containing a pressurized fluid, the pressurized fluid having a first pressure, the reservoir being part of an apparatus comprising a housing, a housing coupler, and a housing sealing element;
passing the pressurized fluid through at least one pressure regulation stage to produce pressurized fluid at a regulated pressure, the regulated pressure being lower than the first pressure, the at least one pressure regulation stage comprising a continuously variable pressure controller contained within the housing, the continuously variable pressure controller being in fluid communication with the reservoir containing the pressurized fluid when the reservoir is in an open state;
moving an actuator, the actuator being mechanically coupled to the continuously variable pressure controller of the at least one pressure regulation stage, along an axis of motion to control the regulated pressure, the regulated pressure being linearly and continuously dependent on an amount of movement of the actuator along the axis of motion for at least a portion of a range for the axis of motion for increases in the regulated pressure, the regulated pressure being linearly and continuously dependent on an amount of movement of the actuator along the axis of motion for at least a portion of a range for the axis of motion for increases in the regulated pressure;
passing the pressurized fluid at the regulated pressure into a first volume of a dispensing device, the first volume being in fluid communication with a surface of a piston; and
displacing the piston within the dispensing device to inject a viscous fluid contained in a second volume of the dispensing device.

18. The method of claim 17, further comprising:
coupling the dispensing device to the housing, the reservoir of pressurized fluid being at least partially contained within the housing, the dispensing device being coupled to the housing prior to opening the reservoir of pressurized fluid.

19. The method of claim 17, wherein the pressurized fluid in the reservoir having a first pressure comprises at least a condensed phase and a gas phase.

20. The method of claim 17, wherein opening a reservoir containing a pressurized fluid comprises at least one of piercing a wall of the reservoir or opening a valve associated with the reservoir.

* * * * *